(12) United States Patent
Raitzer et al.

(10) Patent No.: US 7,457,654 B2
(45) Date of Patent: Nov. 25, 2008

(54) ARTIFACT REDUCTION FOR VOLUME ACQUISITION

(75) Inventors: Gerald A. Raitzer, Seattle, WA (US); Mervin M. Smith-Casem, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 549 days.

(21) Appl. No.: 10/694,098

(22) Filed: Oct. 27, 2003

(65) Prior Publication Data

US 2005/0090740 A1 Apr. 28, 2005

(51) Int. Cl.
*A61B 8/00* (2006.01)
(52) U.S. Cl. ...................... 600/407; 600/444
(58) Field of Classification Search ......... 600/443–448; 128/916; 74/3.52, 828; 318/119, 450, 453, 318/456, 461, 466–467, 484; 342/422, 428; 347/250; 348/36, 37, 77, 92
See application file for complete search history.

(56) References Cited

U.S. PATENT DOCUMENTS

| | | | | |
|---|---|---|---|---|
| 4,137,777 A | * | 2/1979 | Haverl et al. | 73/620 |
| 4,517,985 A | * | 5/1985 | Teslawski et al. | 600/446 |
| 4,579,122 A | * | 4/1986 | Shimizu et al. | 600/445 |
| 4,581,636 A | * | 4/1986 | Blaker et al. | 348/163 |
| 4,797,749 A | * | 1/1989 | Paulsen | 358/302 |
| 4,805,155 A | * | 2/1989 | Shiraishi et al. | 367/7 |
| 4,896,672 A | * | 1/1990 | O'Toole | 600/445 |
| 5,070,879 A | * | 12/1991 | Herres | 600/444 |
| 5,152,294 A | * | 10/1992 | Mochizuki et al. | 600/459 |
| 5,485,845 A | * | 1/1996 | Verdonk et al. | 600/463 |
| 6,080,108 A | * | 6/2000 | Dunham | 600/459 |
| 6,106,471 A | | 8/2000 | Wiesauer et al. | |
| 6,831,736 B2 | * | 12/2004 | Elichai et al. | 356/237.1 |

FOREIGN PATENT DOCUMENTS

JP 2001070301 A * 3/2001
JP 2002360566 A * 12/2002

OTHER PUBLICATIONS

"Voluson 730—Real-Time 4D," American Lab; http://www/american-lab.com/voluson_730.htm; printed Oct. 16, 2003; pp. 1-3.

* cited by examiner

*Primary Examiner*—Francis J. Jaworski

(57) ABSTRACT

Motion artifacts are reduced for three- or four-dimensional imaging with a mechanically rocked array by determining a position of a scan within a volume as a function of velocity. A represented position within a volume of a mechanically rocked scan is determined. Differences in velocity associated with different scan plane positions are used to alter or adjust a scan position. For example, the start position for a transmit operation or the spatial location represented by previously acquired data is altered as a function of a corresponding velocity in the mechanical movement of the array. Variation in velocity results in different relative scan positions or adjustments within the volume. The velocity variation is determined in an open loop, such as from previously measured or expected velocity of the array, or from feedback from actual measured position and associated velocity of the array.

28 Claims, 2 Drawing Sheets

US 7,457,654 B2

ARTIFACT REDUCTION FOR VOLUME ACQUISITION

BACKGROUND

The present invention relates to three- and four-dimensional medical imaging. Artifacts due to a mechanically rocked array or movement are reduced for volume medical imaging.

In medical diagnostic ultrasound imaging, mechanically rocked arrays are used to acquire information representing a three-dimensional volume. A linear array of elements is mechanically rocked in an elevation dimension to scan different planes within a volume. Acoustic energy is electronically steered along an azimuth dimension for scanning within each of the elevationally spaced planes. Since the array moves over time, the beginning and ending transmit beams within a given elevation plane are offset in the elevation dimension. As a result, a motion artifact is generated when the acquired ultrasound data is used for generating a three-dimensional representation. Where the mechanical velocity is low, the motion artifact is limited. Four dimensional imaging or the generation of a sequence of three-dimensional images representing a volume over time is desired in medical diagnostic ultrasound. For rapidly acquiring data representing a three-dimensional volume, a motion artifact becomes more substantial.

BRIEF SUMMARY

By way of introduction, the preferred embodiments described below include methods and systems for artifact reduction and volume acquisition. A position within a volume of a mechanically rocked scan is determined. Differences in velocity associated with different scan plane positions are used to alter or adjust a scan position. For example, the start position for a transmit operation or the spatial location represented by previously acquired data is altered as a function of a corresponding velocity in the mechanical movement of the array. Variation in velocity results in different relative scan positions within the volume. The velocity variation is determined in an open loop, such as from previously measured or expected velocity of the array, or from feedback from actual measured position and associated velocity of the array.

In a first aspect, a method for determining a position of a scan plane of a mechanically rocked scan within a volume is provided. A velocity variation of the mechanically rocked array is determined. A scan position is adjusted as a function of the velocity variation.

In a second aspect, a system for determining a position of a scan plane of a mechanically rocked scan within a volume is provided. A beamformer connects with a mechanically rocked array. The beamformer is operable to adjust a scan position as a function of a velocity variation of the mechanically rocked array.

In a third aspect, a method for determining a position of a mechanically rocked scan within a volume is provided. A velocity is determined for each of a plurality scan positions. The velocities for at least two of the scan positions are different. Each of the plurality scans are started as a function of the respective velocities and scan positions.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Motion artifacts are avoided or reduced by accounting for variances in velocity of a mechanically rocked array. The elevation start position of electronic scans along the azimuthal dimension is adjusted as a function of velocity of the array. Positional errors or velocity variation result from the electromechanical movement of the array. For example, the acceleration of the array from a stop position is slower than the deceleration of the array to a stop position. As a result, the velocity at a given position in a forward direction of movement of the array may be different than the velocity at the same position in the reverse movement of the array. Variation of the motor speed and unexpected or not ideal array angular velocity may also exist. Velocity variation is corrected by modeling or real-time feedback. The position represented by acquired data or the actual position to scan using ultrasonic transmission and reception is controlled as a function of the velocity variation.

Figure 1:
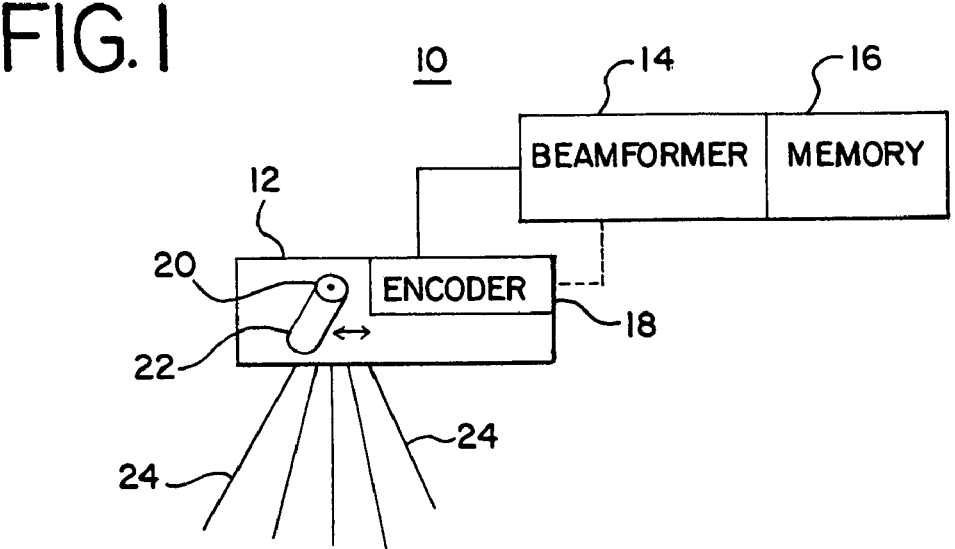
FIG. 1 is a block diagram of one embodiment of a system for determining a position of a mechanically rocked scan within a volume.

FIG. 1 is a block diagram of one embodiment of a system for determining a position of a scan plane of a mechanically rocked scan within a volume. The system 10 includes a mechanically rocked array 12, a beamformer 14 and a memory 16. Additional, different or fewer devices may be provided, such as providing a feedback connection represented by the dashed line from the mechanically rocked array 12 with or without the memory 16. Any of various now known or later developed medical imaging systems using a mechanically rocked array 12 may be used.

The mechanically rocked array 12 is a wobbler array with a motor 20 for moving an ultrasound transducer or transducer array 22. An optional encoder 18 is provided for detecting a position of the motor 20 or transducer array 22. The motor 20 is a piezoelectric, stepper, electric, hydraulic, pneumatic or any other now known or latter developed motor for moving the array 22 in at least one direction. A mechanical linkage is provided in one embodiment for causing the array 22 to move in forward and reverse directions as represented by the arrows adjacent to the array 22 in FIG. 1. Alternatively, the motor 20 is operated in reverse and forward modes. In response to a control circuit, the motor speed and position are varied during volume scanning. As the motor 20 positions the array 22 at different locations, ultrasound data is acquired. For example, the array 22 is a linear array of elements for electronic steering along the azimuth dimension. The azimuth dimension is represented by an axis orthogonal to the plane of the FIG. 1. The scan planes 24 along the azimuth dimension are represented by the lines 24. The array 22 is operable to scan at different base scan plane positions 24 spaced along an elevation dimension. Due to elevation motion during the acquisition of a scan plane, the starting scan position is at a different elevation position than the ending scan position of a given scan plane.

The beamformer 14 is a transmit, receive or both transmit and receive beamformer. Any of analog or digital beamformers may be used. Any now known or later developed beamformer for operation with a mechanically rocked array 12 may be used. In one embodiment, the beamformer 14 is operable to generate beams of acoustic energy, but plane wave transmission of acoustic energy may be used with the beamformer 14. The beamformer 14 includes a plurality of channels with associated delays and amplifiers for electrically steering beams of acoustic energy using delay and apodization profiles. The channels are connected to respective elements of the array 22 for electronically steering along the azimuth dimension.

In one embodiment, the beamformer 14 includes control circuits for timing the transmission and reception of acoustic energy from the array 22 as a function of elevation velocity. Alternatively, timing circuits are provided separate from the beamformer 14, such as in the array 12. The beamformer 14 is operable to adjust a scan plane position as a function of velocity variation of the mechanically rocked array 12. A transmit position for the start of a planar scan is adjusted as a function of velocity variation in one embodiment. The start positions for different scan planes are varied as a function of different velocities. Scanning associated with higher velocity movement of the transducer array 22 start at elevation positions further away from a base position than scanning associated with lower velocities. For example, a first scan plane is associated with a lower velocity, so less elevation distance is traveled by the array 22 from the beginning scan line to a middle or other scan line within the planar scan. For a base scan plane position in the center of the volume, the scan is associated with higher velocity movement of the transducer array 22. The starting scan line is transmitted earlier relative to the middle or other scan line of that scan plane to account for the greater velocity. As another example, the transducer array 22 moves at a different speed for the reverse direction than the forward direction at a given location, such as for a base scan plane 24 positioned on the edges of the volume. Where the forward and reverse scans are intended to scan a similar or same scan plane, the scan position is adjusted as a function of the speed so that one or more scan lines or positions of the forward scan plane and reverse scan plane are aligned. The start scan position is different for the scan in the forward direction than for the scan in the reverse direction to scan the same base position 24 due to the difference in direction and associated difference in velocity. The start position is further away from the desired scan plane position for higher velocities than for lower velocities.

In one embodiment, the array velocity at each scan plane position is determined in real time using feedback from the encoder 18. In an alternative embodiment, the velocity is modeled and provided by the memory 16.

The memory 16 is a random access memory, read only memory, digital memory, analog memory, or any other now known or later developed device for storing an array velocity profile or other velocity information. In an alternative embodiment, the memory 16 is a circuit for calculating or generating a representation of the velocity, velocity profile or identifying locations associated with a velocity variation, velocity or other movement characteristic of the mechanically rocked array 12. The memory 16 is connected with the beamformer 14 as part of or as a separate device from the beamformer 14. In one embodiment, the memory 16 stores an array velocity profile representing speed or velocity of the array as a function of position or time. The velocity profile is stored for both forward and reverse directions, but may be stored for only forward or only reverse direction of movement. Typically, the velocity profile for forward movement of the array is different than for reverse movement of the array.

The encoder 18 is a digital or analog circuit for measuring a position of the motor 20, linkage or the array 22. In one embodiment, the encoder 18 is an optical sensor for determining a number of rotations and direction of movement of the mechanical linkage, the motor 20 or the array 22. In other embodiments, a magnetic sensor, contact sensor, capacitive sensor, resistance sensor, or other now known or later developed device is provided for encoding the position of the array 22, the motor 20 and/or the mechanical linkage. The encoder 18 outputs an analog or digital signal to the beamformer 14 or other array controller for feedback.

Figure 2:
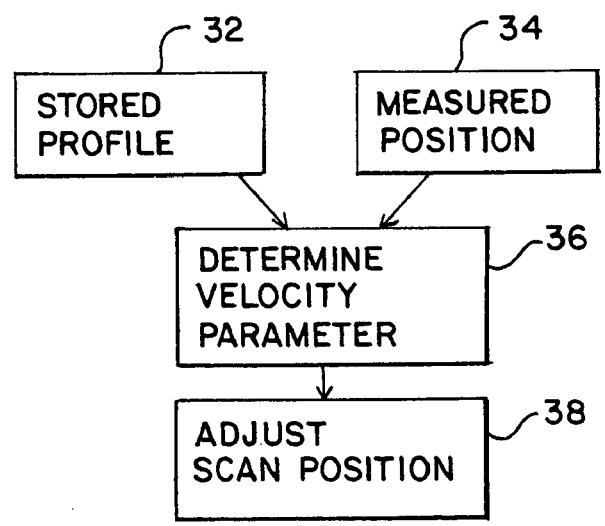
FIG. 2 is a flow chart of one embodiment of a method for determining a position of the mechanically rocked scan within a volume.

FIG. 2 shows a flow chart of one embodiment of a method for determining a position of a scan plane of a mechanically rocked scan within a volume. Using a stored profile provided in act 32 and/or a measured position provided in act 34, a velocity parameter is determined in act 36. The scan position is then adjusted as a function of the velocity parameter in act 38. Additional, different or fewer acts may be provided.

As the array 22 of FIG. 1 is mechanically swept or rotated to scan the volume, frames of data are ultrasonically acquired at predicted or desired positions (i.e., based frame positions). The scan includes narrow and/or wide angle transmissions in any format. FIG. 1 shows five such positions by the scan planes represented by the lines 24. The array 22 is swept in a forward direction, a reverse direction or both a forward and reverse direction to acquire one set of data representing the volume for three- or four-dimensional imaging.

The velocity parameter of act 36 is determined as a function of a stored profile, measured position or both stored profile and measured position. For example, a stored velocity profile is acquired in act 32. The stored velocity represents an expected or programmed velocity, a previously measured velocity profile for the particular motor 20, a previously measured profile for a type of motor or other profile. The previous measurements are after manufacture, before sale, before an imaging session or other time. The velocity parameter of act 36 is then determined as a function of the profile and time. Based on a start time and known or likely position of the array 22, the velocity is determined from the profile. Alternatively, the profile is used in conjunction with a measured position determined in act 34. Using the encoder 18, the current position of the array is measured. The velocity parameter is determined in act 36 by referencing the current position and direction of travel with the stored profile. As yet another example, a measured position is acquired in act 34. The position information and associated time between different positions or scans is used to determine a current velocity in act 36.

Using the stored velocity or other profile, the measured position, or other inputs, a velocity is determined for each of a plurality of scan positions in act 36. Any of various velocity parameters, including speed, linear velocity, angular velocity, distance as a function of time, acceleration, deceleration, change in distance, position with distance and time or other velocity parameter showing the velocity profile of a mechanically rocked array is determined in act 36. A velocity is determined for each of the scan plane positions 24. Some scan plane positions 24 may be associated with a same velocity as other scan plane positions. In one embodiment, the velocity for each scan plane position 24 is provided for both a forward and reverse direction, but may be a same velocity.

Figure 3:
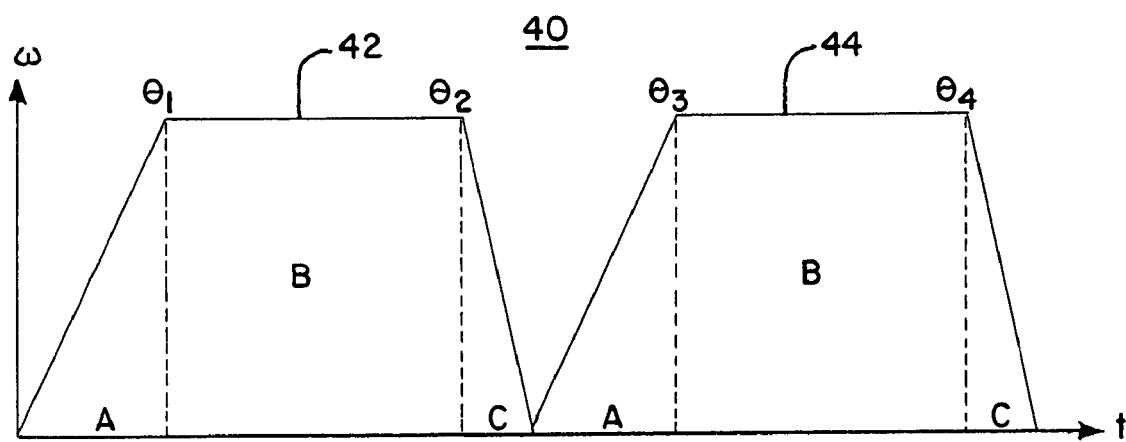
FIG. 3 is a graphic representation of one embodiment of forward and reverse velocity profiles of a mechanically rocked array.
Figure 4:
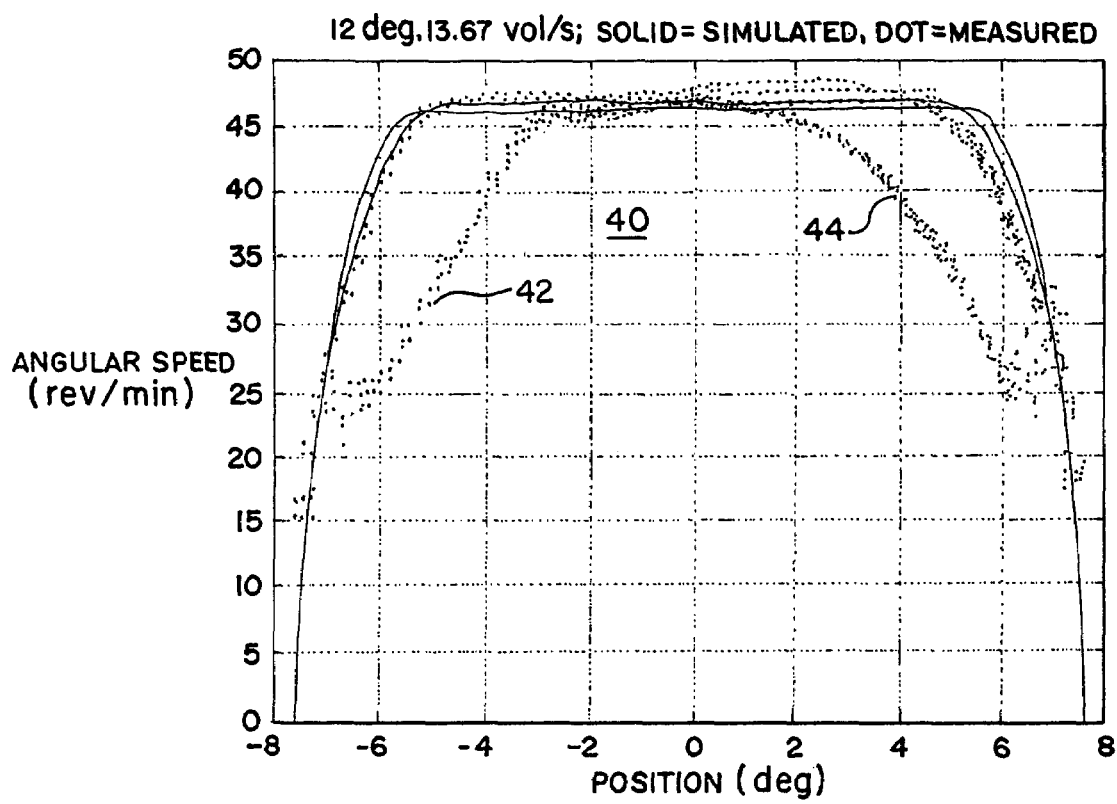
FIG. 4 is a graphical representation of a measured velocity profile of a mechanically rocked transducer array of one embodiment.

In one embodiment, the velocity parameter is determined in act 36 as a function of an array velocity profile 40 shown in FIGS. 3 and 4. FIG. 3 shows an expected or programmed velocity profile 40, and FIG. 4 shows a measured velocity profile 40. The profile 40 includes a forward direction profile 42 and a reverse direction profile 44 representing the same elevation angles or positions. Alternatively, only a forward direction profile 42, only a reverse direction profile 44 or a single profile 40 with one peak is provided. Other profiles 40 may have additional velocity peaks or variation. In one embodiment, a single profile 40 is provided for a mechanically rocked array 12, but a plurality of different profiles for the mechanically rocked array 12 may be provided. For example, the volume scan rate, acoustic frame acquisition parameters or other scan values are used to select a particular velocity profile 40.

As shown in FIGS. 3 and 4, the acceleration from 0 angular velocity to a constant value or substantially constant angular velocity value has a slower change in velocity than the deceleration from a peak or substantially constant angular velocity to no movement. While represented as linear in FIG. 3 for the programmed speed, a non-linear variation may be provided as shown in FIG. 4. The non-linear variation is either programmed or measured.

In one embodiment represented by FIG. 3, the angular speed is estimated from the model programmed into the controller of the motor 20. The angular speed profile is then used to compensate for difference in rotational speed between forward and reverse volume acquisitions or between scan plane positions associated with different speeds.

Due to the limitations of the physical motor control, the motor 20 and associated array 22 may not track identically with the programmed or expected velocity profile 40 of FIG. 3. The difference between predicted and actual angular array velocities may cause undesired artifacts in some embodiments that may be acceptable in other embodiments. As an alternative, the velocity profile is recorded during or after manufacture for a particular motor or type of motor as represented in FIG. 4. The example in FIG. 4 shows that the angular speed during the acceleration phase is in general lower than during the deceleration phase. For example, at −6 degrees, the measured angular speed during acceleration is about 25 rpm. The measured angular speed during deceleration is about 40 rpm. The programmed, expected or modeled angular speeds are about 42 to 43 rpm. Other mechanically rocked arrays 12 and associated forward, reverse or total profiles with the same or different values may be used. This previously measured velocity profile or trajectory data is obtained from storage and used for adjusting a scan position. Measured values from laboratory experiments are loaded onto an ultrasound system using data files or other memory. Storing a measured profile may compensate for systematic differences between a theoretical trajectory and an actual trajectory caused by the motor controller, linkage, array 22, motor 20 or other factor.

In another embodiment, the velocity of the mechanically rocked array 12 is measured during use of the array, such as in a closed loop feedback system. In one embodiment, the velocity is measured directly. In other embodiments, measured positions during use are used to determine a velocity. For example, the array position is measured multiple times during scanning. An amount of time between each of the measurements or associated positions is determined, such as from a system clock. The velocity of the array at each of the positions or between each of the positions is then calculated. The velocity of the array 22 at a particular position is an average of the velocity before and after the position in one embodiment, but may be determined from a single value or other values. In one embodiment, the position measured is at the end of each frame acquisition, such as the elevation position for the acquisition of the last azimuthally spaced scan line for a frame of data. In one embodiment, the feedback of a current position is used to calculate the velocity for a next scan plane. Alternatively, the measured feedback during use provides velocities for a next or subsequent time that the scan plane is positioned in a similar or same location with the array 22 being moved in the same direction. A most recently measured velocity, a running average of velocities, or other single or combination of velocity values may be used to determine the current velocity for a given position. In one embodiment, the feedback measurement is performed periodically, such as every minute or other time period. The velocities from the measured feedback are then used throughout the rest of the time period. For example, movement of the array 22 for warming up or otherwise testing the mechanically rocked array 12 is also used for measuring the current profile or velocities associated with different positions. The measured velocities or velocity profile is then used for altering scan positions throughout the remainder of the imaging session or continuous use of the mechanically rocked array 12.

In act 38, the scan position is adjusted as a function of a velocity variation or other parameter. Adjusting the scan position includes one or more of adjusting a position associated with a scan line, scan plane, group of scan lines, group of scan planes or other positional representation relative to another scan line, group of scan lines, scan plane, group of scan planes or grid. The scan position is adjusted during use, such as altering or setting the position for transmitting or receiving acoustic energy in one embodiment. The scan position is identified using time or position measurements. For example, given a velocity, the time is used to determine a current position. As another example, an actual position measurement is used to determine current position. In another embodiment, the scan position is adjusted by altering a spatial relationship of previously acquired data as a function of the velocity variation. For example, the spatial relationship between scan lines or scan planes is altered as a function of velocity variation for volume rendering or interpolation of ultrasound data to a three-dimensional grid. The correction due to velocity variance for acquired data is performed as part of or separate from the rendering process. For example, the spatial corrections are performed by interpolation to the three-dimensional grid. As another example, the spatial adjustments are performed by weighting during the rendering process.

Figure 5:
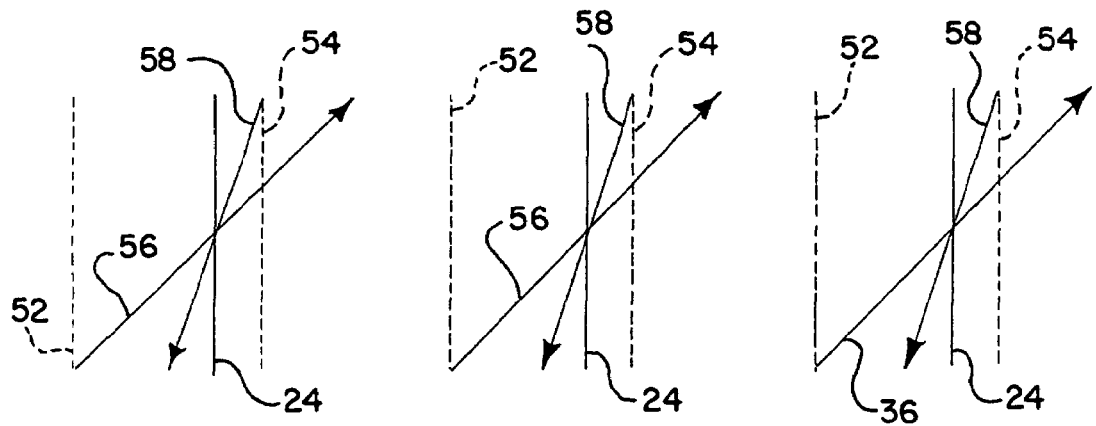
FIG. 5 is a graphical representation of adjustments of scan position in one embodiment.

FIG. 5 is a graphic representation of one embodiment of adjusting scan positions as a function of velocity variation during use. FIG. 5 shows a sequence of desired or base scan plane positions 24 where vertical represents an azimuth axis and horizontal represents an elevation axis. Two or more (e.g., more than the three shown) base scan plane positions 24 may be provided for scanning a volume. For each of the base scan plane positions 24, a start of a scan is determined as a function of the velocity and scan position. For example, a start position or time of a scan with the array moving from the left-to-right direction is indicated by vertical line 52 for scanning relative to the base scan plane position 24. The start of a scan using electronic steering along the azimuth dimension for a frame of data, represented by vertical lines 52 and 54, corresponds to a frame trigger position. The frame trigger position is adjusted as a function of the velocity at a given position. The array 22 is moving in elevation as the scan lines are azimuthally steered from a lower position to an upper position. The ray line 56 indicates the elevation and azimuth position of the scan plane. The ray line 56 may be at a greater or lesser angle to the desired base scan plane position 24. For example, a ray line 58 represents a scan plane starting at the position 54 for a reverse direction or movement of the array 22 from right-to-left in the figure. The ray line 58 has a smaller angle due to a lesser elevation velocity.

The transmit position of at least one scan line, such as the beginning scan line, the ending scan line or other scan line within a acquisition scan plane is adjusted as a function of the velocity. For example, the start of a planar scan is adjusted as a function of the velocity. Where a scan position 24 is associated with a higher velocity, such as in the left-to-right direction for the ray line 56, a planar scan is started earlier than for a lower velocity. For the right-to-left direction, the array travels at a lower velocity such that the distance separating the base scan plane position 24 and the beginning of the planar scan represented by ray line 58 is less than the distance between the beginning of the ray line 56 and the base scan plane position 24. While the example described above shows different velocities associated with different directions of travel of the array, different velocities may be provided for different base scan plane positions 24 along a same direction. For example, the start position 52 for the first scan plane position 24 may be greater or lesser than the start position 52 for a subsequent base scan plane position 24.

As represented in FIG. 5, the center scan line or line of a scan plane is positioned at the base scan plane position 24. As a result, the start position 52, 54 varies as a function of the velocity associated with the base scan plane position 24. In alternative embodiments, other planar positions, such as other than the center along the ray lines 56 or 54, are positioned along the base scan line position 24. By accounting for the velocity at a position or velocity variation over multiple positions, the frame acquisition position 56, 58 is adjusted to account for varying speed of the array through the wobble trajectory. The adjustment of the frame acquisition positions 56, 58 may reduce motion artifacts. In one embodiment, each of the base positions 24 are equally spaced, but base positions with different spacing or spacing variation may be provided.

In one embodiment, the base scan positions 24 and scan planes 56 in a given direction are independent of the corresponding base scan plan position 24 and scan planes 58 in the other direction. In alternative embodiments, the base scan plane positions 24 in one direction are positioned to avoid any overlap with base scan plane positions 24 in another direction. In yet another alternative embodiment, the base scan plane positions 24 of a scan in one direction are aligned with base scan plane positions 24 of a scan in another direction. For example, at least one scan line of a reverse direction scan is aligned with the scan line of a forward direction scan as represented in FIG. 5. The transmit position of the start of each planar scan is adjusted as a function of the velocity such that the base scan line (e.g., center scan line) is at a same position (e.g. the base scan line 24) in both the forward and reverse direction scans of the array 22. Where the velocity is different in the forward and the reverse direction, the start position of each scan is spaced a different distance or started at a different time relative to the base scan line position 24. For example, the separation from the start position 52 and a base scan line position 24 is greater due to a greater velocity in the forward direction than the space between the base scan line position and the start of the scan position 54 in the opposite direction due to the lower velocity. Given different velocities, different relative spacings between the forward and reverse directions may be provided.

Different scan line positions or locations of overlap may be provided. For example, the start or finish of each of the forward and reverse direction scans is aligned to occur at a same elevation position. The resulting scan provides two parallel planes with no overlap given a same velocity. Overlap may occur at different locations given different velocities. Any of various possible alignments may be provided for having some or no overlap.

By adjusting the frame acquisition positions as a function of velocity across the elevation axis, the center vectors of the frame of the forward and reverse volume scans may coincide to reduce motion artifacts. By alternating the scan direction of the wobbling array 22 and aligning the forward and reverse frames for transmit and receive operation in opposite directions across the array with center alignment, the resulting frames are more parallel, have more overlap or represent more of a same plane. The amount of coincident scanning of a same base plane position in the volume is maximized.

While FIG. 5 shows starting a scan on opposite azimuth sides for reverse and forward scanning, different scan formats, such as with the first transmit beam being other than at the edge of the scan plane, may be provided for either or both of the directions. Each frame acquisition position is adjusted such that the frame sequence begins early enough that the middle vector or other assigned scan line is transmitted when or near the array position corresponds to the base frame position 24. While FIG. 5 represents the scan plane as linear vectors 56 and 58, the scan planes may curve due to a variation in velocity of the movement of the array 22 in elevation during the electrically steered acquisition of data in the azimuthal dimension.

The angular speed for each trigger position or start of a scan is interpolated from measured or profile velocity information. The speed versus position information is used to interpolate the angular speed at each base frame position 24 where the velocity does not correspond to the exact same position. Using a calculated angular speed table or a processor for calculating the angular speed, the ultrasound system estimates the frame position adjustment to ensure that the center vector or scan line is fired at the desired position. The distance that the array travels for one frame period may be used to estimate the frame position adjustment needed to ensure the center or other beams of the frame from the forward and reverse volumes coincide. The frame position at the beginning of a frame acquisition is known by measurement or timing, so that the distance that array travels during the frame period may be calculated by subtracting the initial position from the final position. The final position is determined by the known velocity or time for performing a scan. For example, the trigger period or start of acquisition for each frame of data is adjusted by half the distance the array travels during one frame period at the particular frame position. The adjustment is based on velocity variation between different base frame positions 24 assuming a linear velocity throughout the acquisition period for the given frame. In alternative embodiments, a non-linear velocity or variation of velocity is accounted for during the acquisition of a given frame of data or planar scan.

As yet another example, relative velocity between the transducer and the patient is measured and data acquired using the mechanically rocked array 12 or a two-dimensional array is adjusted as a function of the velocity. The scan acquisition position may also be adjusted as a function of the velocity.

While the invention has been described above by reference to various embodiments, it should be understood that many changes and modifications can be made without departing from the scope of the invention. For example, different scan formats may be for electronic steering. As another example, scan line or vector positions other than the center vector of a scan may be aligned to a desired or base position. Velocity variation during an electronic scan in the azimuth dimension, velocity variation from one base scan position to another base scan position for sequential or different planar scans, velocity variation between reverse and forward directions, and/or combinations thereof may be used for adjusting scan position.

It is therefore intended that the foregoing detailed description be regarded as illustrative rather than limiting, and that it be understood that it is the following claims, including all equivalents, that are intended to define the spirit and the scope of this invention.

We claim:

1. A method for determining a position of a mechanically rocked scan within a volume, the method comprising:
    (a) determining first and second velocity parameters of a mechanically rocked array at first and second different positions, respectively, the velocity parameter being different at each of the first and second positions; and
    (b) setting first and second scan positions as a function of the first and second velocity parameters, respectively;
    wherein (a) comprises storing an array velocity parameter profile having the velocity parameters for various scan plane positions throughout the volume scan, the various scan plane positions including the first and second positions.

2. The method of claim 1 wherein (a) comprises storing the array velocity parameter profile for both the forward and reverse directions of the mechanically rocked array, the forward array velocity parameter profile different than the reverse velocity parameter profile.

3. The method of claim 2 further comprising:
    (c) measuring the array velocity parameter profile prior to use by a customer.

4. The method of claim 2 further comprising:
    (c) predicting the array velocity parameter profile from a programmed motor speed.

5. The method of claim 1 wherein (a) comprises measuring velocity of the mechanically rocked array during use and wherein (b) comprises setting during the use.

6. The method of claim 5 wherein (a) comprises:
    (a1) measuring positions of the array during a scanning operation;
    (a2) determining an amount of time between positions; and
    (a3) calculating a velocity of the array at each of the positions.

7. The method of claim 1 wherein (b) comprises setting a transmit position of at least one scan line.

8. The method of claim 7 wherein (b) comprises setting the transmit position of a start of a planar scan.

9. The method of claim 8 wherein (b) comprises setting the transmit position of the start of the planar scan such that a base scan line is at a same position in both forward and reverse direction scans of the array.

10. A method for determining a position of a mechanically rocked scan within a volume, the method comprising:
    (a) determining first and second velocity parameters of a mechanically rocked array at first and second different positions, respectively, the velocity parameter being different at each of the first and second positions; and
    (b) setting first and second scan positions as a function of the first and second velocity parameters, respectively;
    wherein (b) comprises varying start positions for different scan planes as a function of different velocities including the first and second velocities, scan planes associated with higher velocities starting at elevation positions further away from a center scan line position than scan planes associated with lower velocities.

11. The method of claim 10 wherein (a) comprises using an array velocity parameter profile having the velocity parameters, including the first and second velocity parameters, for various scan plane positions through the volume scan, the various scan plane positions including the first and second positions, wherein the array velocity parameter profile is predicted from a programmed motor speed.

12. The method of claim 10 wherein (a) comprises using an array velocity parameter profile having the velocity parameters, including the first and second velocity parameters, for various scan plane positions through the volume scan, the various scan plane positions including the first and second positions, wherein the array velocity parameter profile is measured.

13. A method for determining a position of a mechanically rocked scan within a volume, the method comprising:
    (a) determining first and second velocity parameters of a mechanically rocked array at first and second different positions, respectively, the velocity parameter being different at each of the first and second positions; and
    (b) setting first and second scan positions as a function of the first and second velocity parameters, respectively;
    wherein a forward direction velocity of the array is different than a reverse direction velocity for the first position, the first velocity being the forward direction velocity, and
    wherein (b) comprises aligning a forward direction scan plane relative to a reverse direction scan plane as a function of the forward and reverse direction velocities.

14. The method of claim 13 wherein (a) comprises using an array velocity parameter profile having the velocity parameters, including the first and second velocity parameters, for various scan plane positions through the volume scan, the various scan plane positions including the first and second positions, wherein the array velocity parameter profile is predicted from a programmed motor speed.

15. The method of claim 13 wherein (a) comprises using an array velocity parameter profile having the velocity parameters, including the first and second velocity parameters, for various scan plane positions through the volume scan, the various scan plane positions including the first and second positions, wherein the array velocity parameter profile is measured.

16. A system for determining a position of a mechanically rocked scan within a volume, the system comprising:
    a mechanically rocked array;
    a beamformer operable to set first and second scan positions as a function of first and second different velocity parameters, respectively, of the mechanically rocked array; and
    a memory connected with the beamformer, the memory operable to store an array velocity profile having velocity parameters including the first and second velocity parameters for various scan plane positions throughout the volume scan.

17. The system of claim 16 wherein the memory is operable to store the array velocity profile for both forward and reverse directions of the mechanically rocked array, the forward array velocity profile different than the reverse velocity profile, the beamformer operable to set the scan positions including the first and second scan positions differently for the reverse direction than for the forward direction.

18. The system of claim 17 wherein said array velocity parameter profile is predicted from a programmed motor speed.

19. The system of claim 10 further comprising:
an encoder connected with the array;
wherein the beamformer is operable to determine an array velocity parameter in response to inputs from the encoder.

20. The system of claim 16 wherein the beamformer is operable to set a transmit position of a start of a planar scan as a function of the first velocity parameter.

21. The system of claim 16 wherein said array velocity parameter profile is predicted from a programmed motor speed.

22. A system for determining a position of a mechanically rocked scan within a volume, the system comprising:
a mechanically rocked array; and
a beamformer operable to set first and second scan positions as a function of first and second different velocity parameters, respectively, of the mechanically rocked array;
wherein the beamformer is operable to vary start positions for different scan planes as a function of different velocities, scan planes associated with higher velocities starting at elevation positions further away from a center scan line position than scan planes associated with lower velocities.

23. The system of claim 22 wherein said first and second velocity parameters are from an array velocity parameter profile predicted from a programmed motor speed.

24. A method for determining a position of a scan plane of a mechanically rocked scan within a volume, the method comprising:
(a) determining a velocity parameter for each of a plurality of scan positions, the velocity parameters for at least two of the scan positions being different; and
(b) starting each of a plurality of scans as a function of the respective velocity parameters and scan positions;
wherein (a) comprises determining from a stored velocity profile.

25. The method of claim 24 wherein (a) comprises determining from a measured position during use.

26. The method of claim 24 wherein (b) comprises starting planar scans earlier relative to the respective scan position for higher velocities than for lower velocities.

27. The method of claim 24 wherein (b) comprises aligning a position of at least one scan line of a reverse direction scan with a forward direction scan.

28. The system of claim 24 wherein said stored velocity profile is predicted from a programmed motor speed.

* * * * *

UNITED STATES PATENT AND TRADEMARK OFFICE
CERTIFICATE OF CORRECTION

| | |
|---|---|
| PATENT NO. | : 7,457,654 B2 |
| APPLICATION NO. | : 10/694098 |
| DATED | : November 25, 2008 |
| INVENTOR(S) | : Gerald A. Raitzer and Mervin M. Smith-Casem |

It is certified that error appears in the above-identified patent and that said Letters Patent is hereby corrected as shown below:

Column 11, line 4, cancel the text "19. The system of claim 10", and insert the --19. The system of claim 16--.

Signed and Sealed this

Third Day of November, 2009

David J. Kappos
*Director of the United States Patent and Trademark Office*